US00PP33477P2

(12) United States Plant Patent
Whitaker

(10) Patent No.: US PP33,477 P2
(45) Date of Patent: Sep. 14, 2021

(54) STRAWBERRY PLANT NAMED 'FL 16.78-109'

(50) Latin Name: ***Fragaria* X *ananassa* Duchesne**
Varietal Denomination: FL 16.78-109

(71) Applicant: Florida Foundation Seed Producers, Inc., Marianna, FL (US)

(72) Inventor: Vance M. Whitaker, Brandon, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/985,149

(22) Filed: Aug. 4, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

PP25,574 P3 5/2015 Whitaker et al.
PP30,564 P3 6/2019 Whitaker

OTHER PUBLICATIONS https://www.tampabay.com/arts-entertainment/food/2020/03/02/the-scientist-making-florida-strawberries-bigger-sweeter-and-sometimes-grape-flavored/; Mar. 2, 2020; 9 pages.*
U.S. Appl. No. 16/985,155, filed Aug. 4, 2020, Whitaker.

* cited by examiner

*Primary Examiner* — Kent L Bell
(74) *Attorney, Agent, or Firm* — Dentons US LLP

(57) ABSTRACT

A new and distinct variety of strawberry (*Fragaria* X *ananassa*), which originated from seed produced by a hand-pollinated cross between 'FL 12.90-53' and 'FL 14.29-62'. The new strawberry, named 'FL 16.78-109', can be distinguished at least by its white internal fruit color when fully ripe; white to light pink external fruit color when fully ripe; consistent conical shape; and low acid content when grown in West Central Florida or other regions that have a climate similar to that of West Central Florida.

2 Drawing Sheets

Latin name of the genus and species of the plant claimed: *Fragaria* X *ananassa* Duchesne.

Variety denomination: 'FL 16.78-109'.

BACKGROUND OF THE INVENTION

The present invention relates to a new and distinct variety of strawberry plant (*Fragaria* X *ananassa* Duchesne) named 'FL 16.78-109'. This new strawberry plant is distinguished at least by its ability to produce fruit that have white internal color and white to light pink external color when fully ripe, consistent conical shape, and a unique flavor arising partly from low acid content when grown in West Central Florida. Asexual propagation of 'FL 16.78-109' was performed at Balm, Fla., which is also where the selection was made and the plants were tested. 'FL 16.78-109' can be contrasted with 'Florida Brilliance' (U.S. Plant Pat. No. 30,564) and 'Florida127' (U.S. Plant Pat. No. 25,574), which are the current, dominant strawberry varieties in Hillsborough County, Fla. 'FL 16.78-109' is a promising candidate for commercial success because it produces fruit that are white to light pink in color when fully ripe throughout the entire Florida market window.

SUMMARY OF THE INVENTION

'FL 16.78-109', when grown in a subtropical climate during the fall, winter, or a combination thereof, can be distinguished from all other strawberry plants by at least the following characteristics: white internal fruit color when fully ripe; white to light pink external fruit color when fully ripe; consistent conical shape; and low acid content.

'FL 16.78-109' originated in a strawberry breeding plot in Balm, Fla. The seed parent was 'FL 12.90-53', an unreleased, unpatented breeding selection with excellent fruit size and yield. The pollen parent was 'FL 14.29-62', an unreleased, unpatented breeding selection with white internal color and white to light pink external color when ripe. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 16.78-109' was selection number 109 of the 78$^{th}$ cross in the 2016-2017 seedling trial, and thus was given the breeding trial designation of 'FL 16.78-109'. 'FL 16.78-109' exhibited unique white to light pink fruit color when fully-ripe, excellent shape and sweet flavor. 'FL 16.78-109' has been asexually propagated annually by runners; and test plantings have established that the vegetative and fruit characteristics of the propagules are identical to those of the initial daughter plants.

'FL 16.78-109' can be distinguished from its seed parent 'FL 12.90-53' at least by its white to light pink fruit color and sweeter fruit flavor. 'FL 16.78-109' is believed to be phenotypically most similar to its pollen parent. Nonetheless, 'FL 16.78-109' can be distinguished from its pollen parent 'FL 14.29-62' at least by its larger fruit size and more consistent conical shape.

Currently, 'Florida Brilliance' (U.S. Plant Pat. No. 30,564) and 'Florida127' (U.S. Plant Pat. No. 25,574), are the two dominant strawberries varieties in Hillsborough County, Fla. 'FL 16.78-109' can be distinguished from both due to its white to light pink fruit color when fully ripe (FIGS. 1 & 2) and its lower fruit acid content leading to a unique, sweet flavor.

'FL 16.78-109' is more resistant to *Phytophthora* root and crown rot (caused by *Phytophthora cactorum*) than both commercial standards but is more susceptible to anthracnose fruit rot (caused by *Colletotrichum acutatum*) than both commercial standards.

BRIEF DESCRIPTION OF THE DRAWINGS

'FL 16.78-109' is illustrated by the accompanying photographs of 5-month-old specimens taken in February, 2020. The colors shown are as true as can be reasonably captured by conventional photographic procedures.

DETAILED BOTANICAL DESCRIPTION

Figure 1:
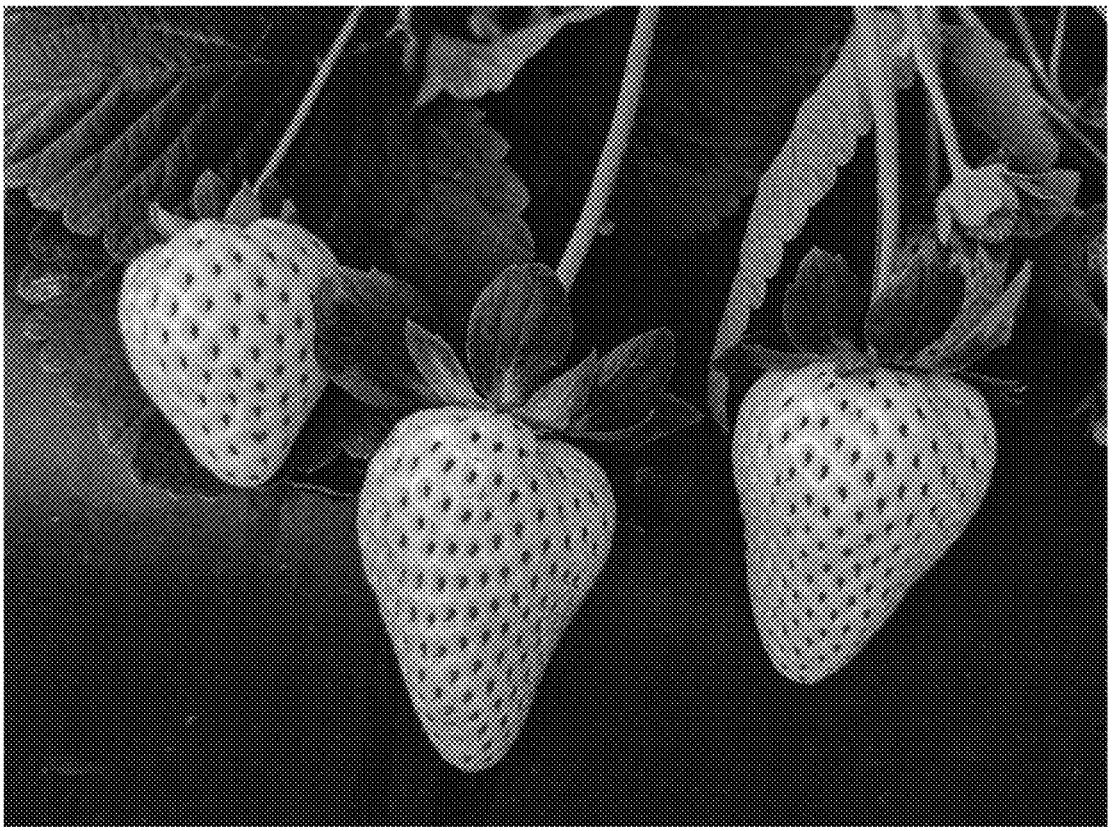
FIG. 1. Shows ripe fruit with white skin with a pink blush and red achenes, pedicels and leaves from 5-month-old specimens in February, 2020 near Dover, Fla.
Figure 2:
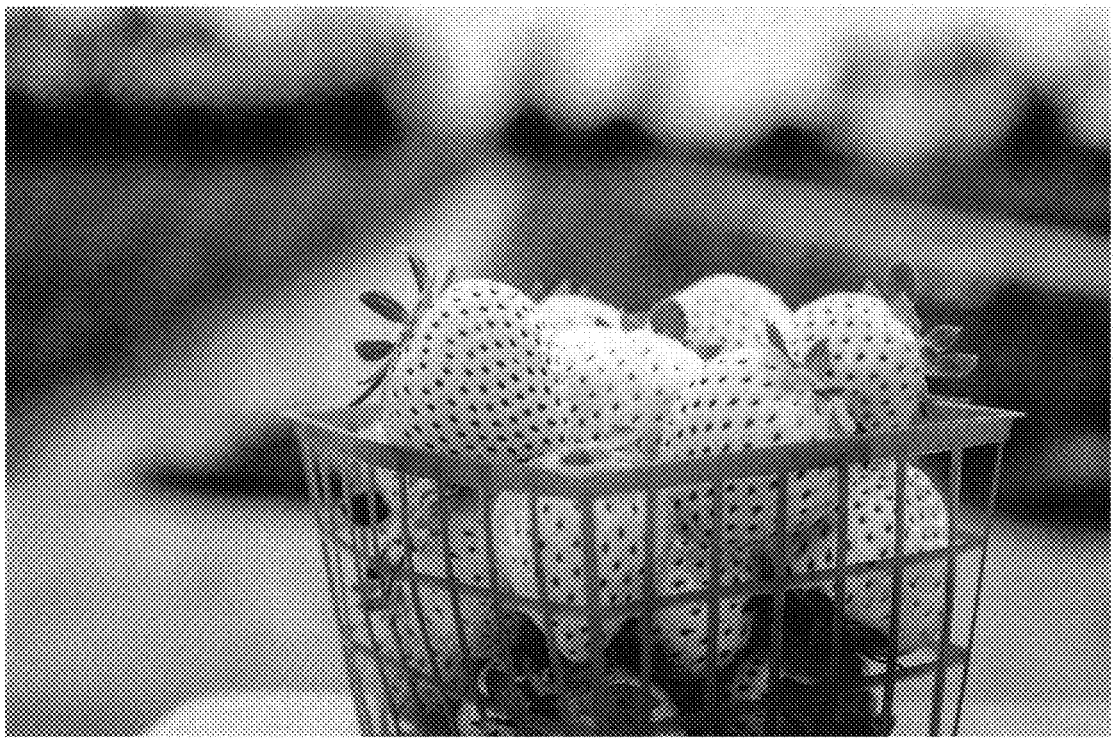
FIG. 2. Shows ripe fruit with white skin with a pink blush and red achenes, harvested from 4-month-old specimens in January, 2020 near Balm, Fla.

The following detailed botanical description sets forth the distinctive characteristics of 'FL 16.78-109'. The present botanical description is of 'FL 16.78-109' when grown under the ecological conditions that prevail during the winter production season in Balm, Fla., i.e., warm days and cool nights. The plant was 5 months of age when the data was collected. Colors are objectively described using the CIELAB color scale (originally published by the International Commission on Illumination (CIE) in 1976) as measured using a Minolta Chroma Meter CR-400 (Minolta, Ramsey, N.J.) colorimeter with a 1 cm aperture, calibrated against a white tile (Y=85.5, x=0.3164, y=0.3237). When the CIELAB color designations differ from the accompanying photographs, the CIELAB color designations are accurate.

PHENOTYPIC DESCRIPTION OF *FRAGARIA* X *ANANASSA* DUCHESNE 'FL 16.78-109'

Classification:
- *Botanical.*—*Fragaria* X *ananassa* Duchesne.
- *Common name.*—Strawberry.

Parentage:
- *Seed parent.*—'FL 12.90-53'.
- *Pollen parent.*—'FL 14.29-62'.

Plant:
- *Average height.*—16 cm to 22 cm.
- *Average width.*—17 cm to 24 cm.
- *Growth habit.*—Moderately compact, round.
- *Number of crowns per plant.*—4 to 7 depending on seasonal conditions.
- *Vigor.*—Medium.

Leaf:
- *Overall description.*—Pinnately compound with three leaflets.

Petiole:
- *Average length.*—16.8 cm.
- *Average diameter.*—3.5 mm.
- *Pubescence.*—Light.
- *Pubescence density.*—Moderate.
- *Pose of hairs.*—Perpendicular.
- *Texture.*—Smooth.
- *Anthocyanin presence.*—Absent.
- *Color.*—Light green (L*=58.32, a*=−14.94, b*=35.40).

Petiolule:
- *Length.*—Terminal leaflet: 7.0 mm. Lateral leaflets: 4.7 mm.
- *Diameter.*—1.8-2.0 mm.
- *Color.*—Light green (L*=64.66, a*=−8.72, b*=24.83).

Stipule:
- *Length.*—32 mm to 40 mm.
- *Width.*—17-20 mm along the base of the petiole attachment.
- *Anthocyanin presence.*—Exceedingly infrequent.
- *Color.*—Light green (L*=62.56, a*=−17.79, b*=22.95).

Terminal leaflet:
- *Average length.*—73 mm.
- *Average breadth.*—62 mm.
- *Length/width ratio.*—1.18.
- *Shape in cross section.*—Slightly concave.
- *Color, upper surface.*—Medium green (L*=37.16, a*=−13.00, b*=17.69).
- *Color, lower surface.*—Light green (L*=52.67, a*=−13.12, b*=19.28).
- *Glossiness.*—Slight gloss.
- *Base shape.*—Cuneate.
- *Apex descriptor.*—Rounded.
- *Pubescence density.*—Sparse.
- *Texture.*—Moderately smooth.
- *Venation pattern.*—Pinnate.

Secondary leaflets:
- *Average length.*—68 mm.
- *Average breadth.*—58 mm.
- *Length/width ratio.*—1.17.
- *Shape in cross section.*—Slightly concave.
- *Color, upper surface.*—Medium green (L*=36.61, a*=−13.42, b*=17.23).
- *Color, lower surface.*—Light green (L*=52.23, a*=−13.51, b*=19.79).
- *Glossiness.*—Slight gloss.
- *Base shape.*—Oblique rounded.
- *Apex descriptor.*—Obtuse.
- *Pubescence density.*—Sparse.
- *Texture.*—Moderately smooth.
- *Venation pattern.*—Pinnate.

Leaflet margins: Crenate, with an average of 24 and 23 serrations per terminal and secondary leaflet, respectively.

Stolons:
- *Number of daughter plants.*—25 to 45 depending on environmental conditions.
- *Anthocyanin presence.*—Occasional.
- *Thickness.*—2 mm to 3 mm.
- *Pubescence.*—Light.

Inflorescence:
- *Time of flowering.*—Partial remontancy, commencing two weeks after establishment and continually thereafter in suitable climate.

*Flower number per plant.*—45 to 60 flowers over a 4 month Florida growing season.

*Flower height.*—0 to 19 cm above soil surface depending on angle of pedicel.

*Position relative to canopy.*—Flowers open at or slightly below canopy height.

*Branching of the inflorescence.*—At or within 3 cm of the crown.

Petals:

*Number.*—5 to 7.

*Length.*—13 to 15 mm.

*Width.*—12 to 14 mm.

*Shape.*—Orbicular.

*Apex.*—Rounded.

*Base.*—Rounded.

*Margin.*—Smooth.

*Average diameter of the corolla* (*i.e. the petals collectively*).—35 mm.

*Average number of stamens.*—33.

*Color, upper surface.*—White (L*=83.13, a*=−2.12, b*=5.89).

*Color, lower surface.*—White (L*=79.75, a*=−1.40, b*=4.63).

Calyx:

*Diameter.*—38-45 mm.

*Diameter of calyx relative to corolla.*—30% greater in diameter.

*Diameter of calyx relative to the fruit.*—30% less to 30% greater in diameter.

*Insertion of calyx.*—Level to slightly inserted.

*Color.*—Medium green (L*=50.08, a*=−16.81, b*=24.75).

Sepals:

*Number per flower.*—12-14.

*Length.*—16-19 mm.

*Width.*—7-12 mm.

*Apex.*—Subacute to lobed.

*Margin.*—Smooth.

*Color, upper surface.*—Medium green (L*=47.5, a*=−17.41, b*=24.62).

*Color, lower surface.*—Light green (L*=52.67, a*=−16.21, b*=24.85).

Pedicels: Attached to mature primary fruit and 14 cm to 19 cm in length and 1.9 to 2.1 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:

*Number per truss.*—5 to 8.

*Shape.*—Medium conical to cordate.

*Average fruit weight.*—16 to 20 g.

*Weight, primary fruit.*—19 to 32 g.

*Weight, secondary and tertiary fruit.*—10 to 19 g.

*Length, primary fruit.*—40 to 50 mm.

*Width, primary fruit.*—27 to 35 mm.

*Fruit flavor.*—Sweet, low-acid.

*Fruit soluble solids content* (*brix*).—As high as 9.76% in January 2020 (Table 1).

*Fruit cavity.*—Rare.

*Achenes.*—Slightly sunken, 50 to 150 per fruit, at least 75% of which are red in color.

*External fruit color.*—White with light pink blush (a*=12.95).

*Internal fruit color.*—White red (a*=−2.54).

*Evenness of color.*—Pink blush on sun side, most achenes red in color.

*Flesh and skin firmness at full ripe stage.*—Moderately firm.

*Rain damage.*—Similar to 'Florida Brilliance'.

Yield: Lower than commercial standards, approximately ¾.

Preferred planting period: October 10$^{th}$ to October 20$^{th}$ in West Central Florida.

Nursery performance: 'FL 16.78-109' produces slightly more runners than both commercial standards.

Disease resistance:

*Botrytis fruit rot* (*caused by botrytis cinerea*).—Moderately susceptible.

*Powdery mildew* (*caused by podosphaera aphanis*).—Moderately resistant.

*Anthracnose fruit rot* (*caused by colletotrichum acutatum*).—Moderately susceptible.

*Charcoal rot* (*caused by macrophomina phaseolina*).—Moderately resistant.

TABLE 1

Soluble solids content (SSC), pH, titratable acidity (TA) and SSC/TA from four harvests dates.

| Cultivar | SSC (%) | pH | TA (%) | SSC/TA |
|---|---|---|---|---|
| December 2019 | | | | |
| 'Florida Brilliance' | 6.41 b[z] | 3.67 b | 0.81 a | 7.96 b |
| 'Florida127' | 8.68 a | 3.82 b | 0.72 a | 12.13 ab |
| 'FL 16.78-109' | 8.15 a | 4.10 a | 0.56 a | 14.45 a |
| January 2020 | | | | |
| 'Florida Brilliance' | 8.43 a | 3.67 b | 0.82 a | 10.56 b |
| 'Florida127' | 9.09 a | 3.63 b | 0.86 a | 10.54 b |
| 'FL 16.78-109' | 9.76 a | 4.13 a | 0.51 b | 19.16 a |
| February 2020 | | | | |
| 'Florida Brilliance' | 6.14 b | 3.76 b | 0.56 a | 10.87 a |
| 'Florida127' | 7.62 a | 3.75 b | 0.61 a | 12.56 a |
| 'FL 16.78-109' | 7.04 ab | 3.93 a | 0.58 a | 12.31 a |
| March 2020 | | | | |
| 'Florida Brilliance' | 8.28 ab | 3.63 b | 0.82 a | 10.09 b |
| 'Florida127' | 9.63 a | 3.73 b | 0.78 a | 12.34 a |
| 'FL 16.78-109' | 8.03 b | 3.87 a | 0.63 b | 12.78 a |

[z]Mean separations within harvest dates and columns are by Tukey's HSD test, $P \leq 0.05$

What is claimed is:

1. A new and distinct strawberry plant named 'FL 16.78-109' as illustrated and described herein.

* * * * *